United States Patent
Bonacci

(10) Patent No.: US 7,390,313 B2
(45) Date of Patent: Jun. 24, 2008

(54) ANGIOGRAPHIC SYRINGE SUPPORT DEVICE AND COMBINED USE THEREOF WITH AN ANGIOGRAPHIC SYRINGE AND AN ANGIOGRAPHIC INJECTOR

(75) Inventor: Fabrice Bonacci, St. Priest (FR)

(73) Assignee: SEDAT, Irigny (FR)

( * ) Notice: Subject to any disclaimer, the term of this patent is extended or adjusted under 35 U.S.C. 154(b) by 0 days.

(21) Appl. No.: 10/542,989

(22) PCT Filed: Jan. 15, 2004

(86) PCT No.: PCT/FR2004/000075

§ 371 (c)(1),
(2), (4) Date: Jul. 21, 2005

(87) PCT Pub. No.: WO2004/078237

PCT Pub. Date: Sep. 16, 2004

(65) Prior Publication Data

US 2006/0111673 A1    May 25, 2006

(30) Foreign Application Priority Data

Jan. 28, 2003  (FR)  ................................. 03 00927

(51) Int. Cl.
*A61M 1/00* (2006.01)
(52) U.S. Cl. .......................................................... 604/151
(58) Field of Classification Search ................ 604/131, 604/151–154, 181, 218, 533; 600/431, 432
See application file for complete search history.

(56) References Cited

U.S. PATENT DOCUMENTS

| | | | |
|---|---|---|---|
| 5,322,511 A * | 6/1994 | Armbruster et al. | 604/155 |
| 5,535,746 A | 7/1996 | Chapman et al. | |
| 6,368,307 B1 * | 4/2002 | Ziemba et al. | 604/218 |
| 2004/0116893 A1 * | 6/2004 | Spohn et al. | 604/500 |

FOREIGN PATENT DOCUMENTS

| | | |
|---|---|---|
| EP | 893 133 A1 | 1/1999 |
| WO | WO 95/13841 A1 | 5/1995 |
| WO | WO 02/056945 A2 | 7/2002 |

* cited by examiner

*Primary Examiner*—Nicholas D. Lucchesi
*Assistant Examiner*—Theodore J Stigell
(74) *Attorney, Agent, or Firm*—Sughrue Mion, PLLC

(57) ABSTRACT

The support device (3) is adapted to be secured to the front face (4) of the injector, and to position an angiographic syringe (1) having a body (7) that presents an outwardly-directed projection (30), the cross-section of the body at the location of said projection being non-circular. The device which is extended forwards by a cradle (23) for supporting the syringe body, includes an upwardly-open recess (24) that presents firstly a non-circular cross-section that is complementary to a portion of the cross-section of the syringe body at the location of said projection, and secondly an abutment front face for said projection. The recess (24) includes a central portion (31) of circularly-arcuate cross-section, which portion is extended by two diametrically-opposite notches (32).

5 Claims, 4 Drawing Sheets

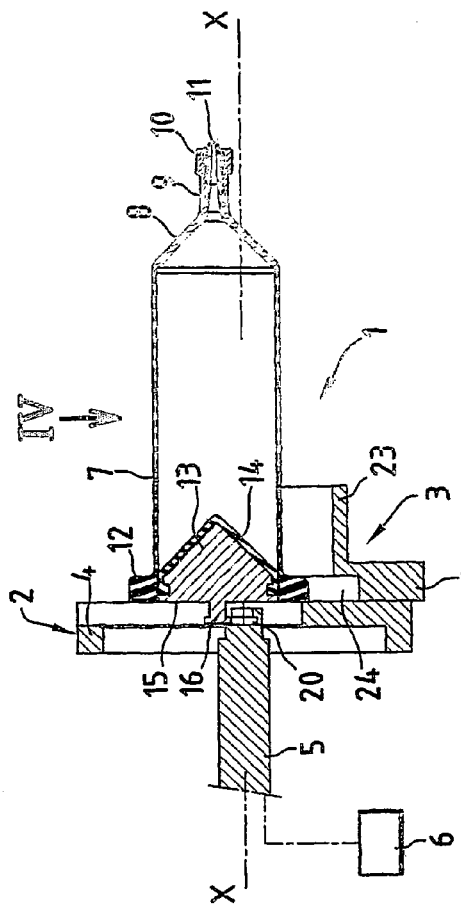
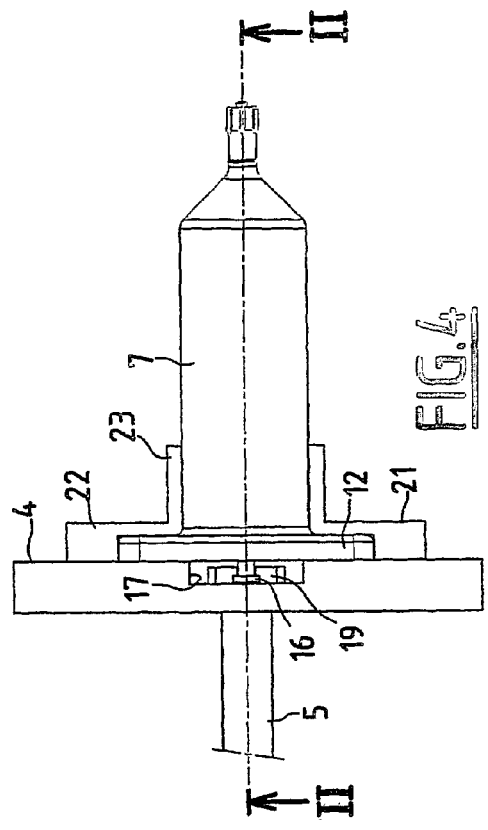
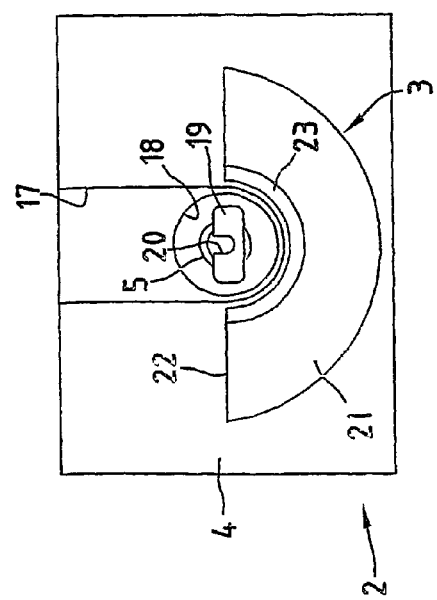
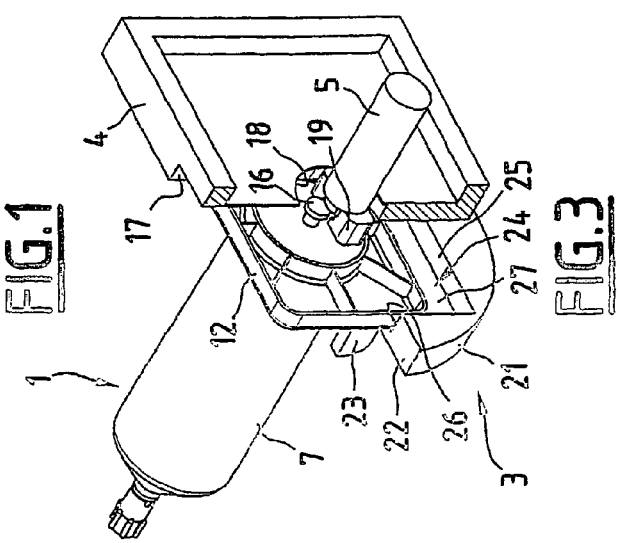

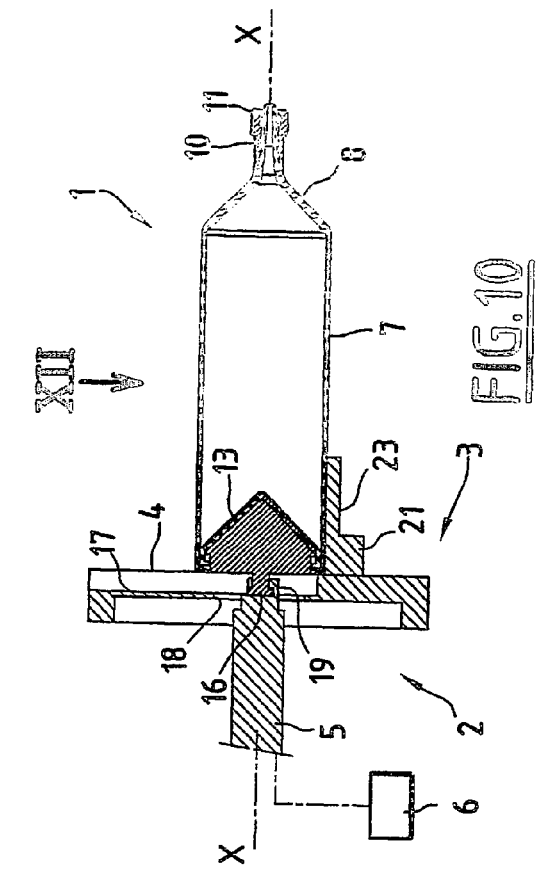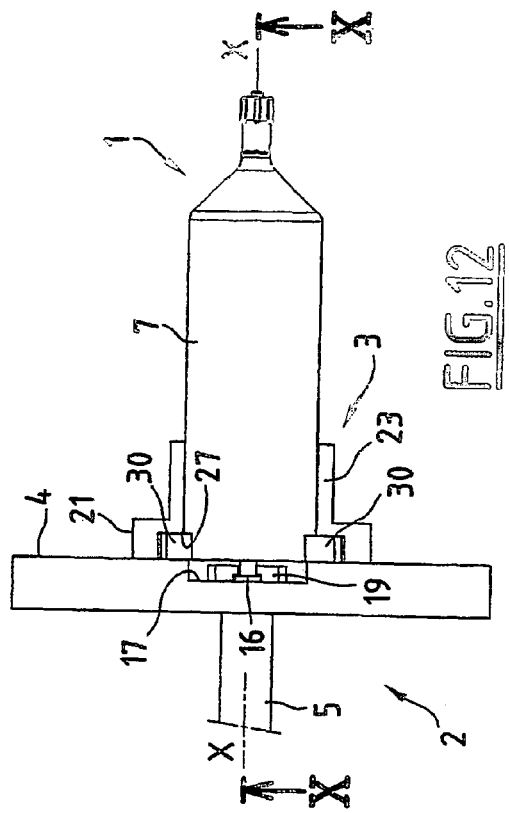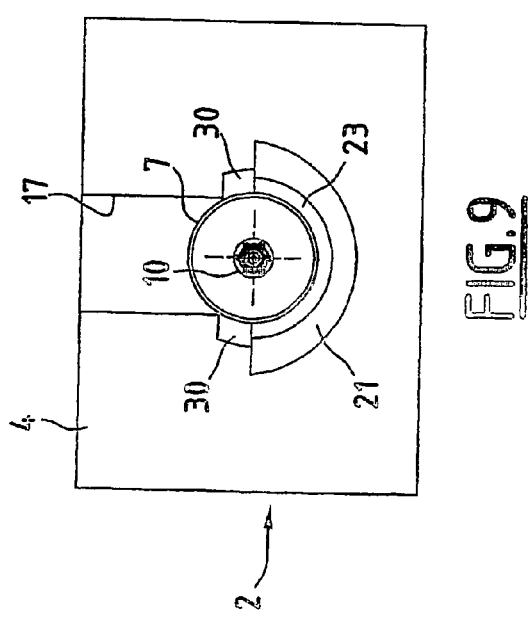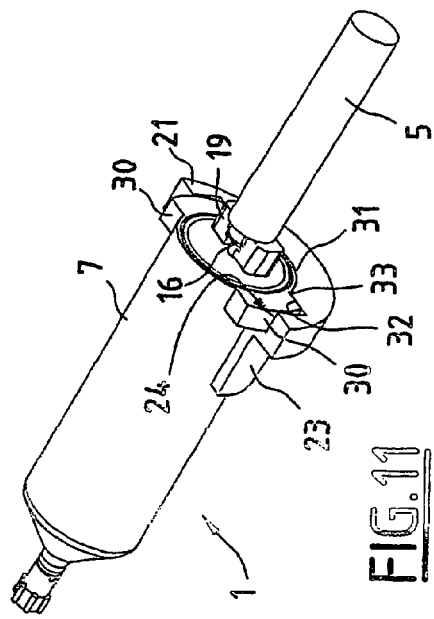

ated radial collar 12, that is substantially rectangular in outside shape.

ANGIOGRAPHIC SYRINGE SUPPORT DEVICE AND COMBINED USE THEREOF WITH AN ANGIOGRAPHIC SYRINGE AND AN ANGIOGRAPHIC INJECTOR

BACKGROUND OF THE INVENTION

The present invention relates to a front-loading syringe support device for an angiographic injector.

The invention relates essentially to the field of injecting contrast media for establishing diagnoses by medical imaging (scanners, magnetic resonance imaging (MRI), and the like).

Front-loading syringes are provided, generally at the rear, with at least one projection projecting from their cylindrical body in order to enable them to be releasably secured to the injector or to a support device secured to the front face thereof. The projection may be a plate (see for example WO-A-02/056947) or a pair of diametrically-opposite tabs (see for example WO-A-97/36635).

Nevertheless, the above arrangements are not entirely satisfactory, either because they do not directly ensure angular positioning of the syringe about its axis, or else because the movement of the syringe on the injector is relatively complex, in particular being of the bayonet type.

WO-A-95/13841 uses a support device in accordance with the precharacterizing portion of claim 1, and provides means for fastening the syringe in a single action serving simultaneously to position the syringe angularly about its own axis. Nevertheless, that prior arrangement does not enable the syringe to be disconnected and withdrawn when the pusher is engaged in the body of the syringe.

SUMMARY OF THE INVENTION

An object of the invention is to eliminate that drawback.

To this end, the invention provides a support device as defined in the claims.

BRIEF DESCRIPTION OF THE DRAWINGS

Examples of embodiments of the invention are described below with reference to the accompanying drawings, in which:

FIG. 1 is a fragmentary diagrammatic front view of an angiographic injection system similar to that of the invention, the syringe not being shown;

FIG. 2 is a fragmentary longitudinal section view of the FIG. 1 system, prior to connecting the syringe, the section being taken on line II-II of FIG. 4;

FIG. 3 is a rear perspective view of the same system;

FIG. 4 is a plan view of the same system seen looking along arrow IV of FIG. 2;

FIGS. 9, 10, and 12 are views of an angiographic injection system in accordance with the invention, respectively as seen from in front, in longitudinal section on line X-X of FIG. 12, and from above, after the syringe has been secured to the injector;

FIG. 11 is a fragmentary perspective view from behind of the system of FIGS. 9, 10, and 12, the front face of the injector being omitted.

DETAILED DESCRIPTION OF THE INVENTION

Figure 5:
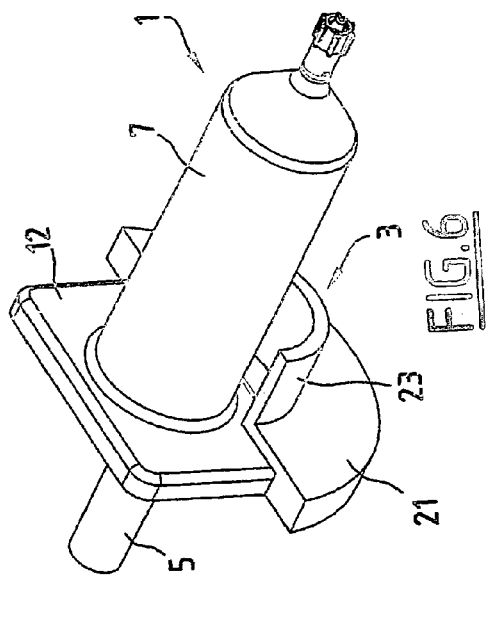
FIGS. 5 and 6 are perspective views of the assembly comprising the syringe, the support device, and the pusher, respectively as seen from behind and front in front, prior to connecting the syringe to the pusher.

The angiographic injection system shown in FIGS. 1 to 8 is essentially constituted by an angiographic syringe 1, an angiographic injector 2, and means, including a syringe support device 3 secured to the front face 4 of the injector, for releasably securing the syringe to the front face 4. The injector includes a pusher 5 that is movable in translation along its axis X-X under the control of control means 6 that are shown very diagrammatically. Only the front face 4 and the pusher 5 of the injector are shown.

The syringe 1 comprises a cylindrical body 7 with a leading portion 8 that converges to an outlet duct 9 fitted with a coupling 10 for a flexible tube 11. The rear end of the body 7 is provided with an outwarldy-directed radial collar 12, that is substantially rectangular in outside shape.

A piston or gasket carrier 13 is placed inside the body 7. The front face of the piston is covered in an elastomer gasket 14 and it is conical in shape, being complementary to the front portion 8 of the body of the syringe. The gasket 14 extends rearwards so as to co-operate with friction against the inside wall of the body. The rear face 15 of the piston is plane, and in its center it has a rearwardly-projecting peg 16, in the form of a mushroom of circular section.

The front face 4 of the injector is plane. It supports a U-shaped recess 17 having a vertical axis and provided at its base with a circular orifice 18 on the axis X-X, adapted to allow the pusher 5 to pass freely therethrough.

The pusher 5, which is mostly of circular section, has a front head 19 of generally rectangular shape with its long sides horizontal. In the top side of this head there is provided a stepped housing 20 that is complementary to the bottom half of the peg 16.

The support device 3 is constituted by a half-disk 21 defined by a horizontal top surface 22 and extending forwards by a semicylindrical cradle 23 that is upwardly open. The half-disk and the cradle are made as a single piece. Over approximately the rear half of its length, the half-disk 21 includes a rearwardly-open recess 24 of cross-section that is complementary to the cross-section of the bottom half of the plate 12 of the syringe when its long sides are horizontal. The recess 24 is thus defined by a horizontal bottom face 25, by two facing vertical walls 26, and by a vertical front face 27. The cradle 23 opens out directly into the front face 27.

The support device 3 is fastened onto the front face 4 of the injector in such a manner that the axis of the cradle 23 coincides with the axis X-X. The bottom outline of the recess 17 then defines the rear wall of the recess 24, which has the same axial length as the plate 12 of the syringe.

The syringe is fastened to the injector as follows.

With the pusher 5 in its retracted position as shown in FIGS. 2 and 3, the bottom long side of the plate 12 of the syringe is placed on the top face of the cradle 23, and the syringe is pushed rearwards.

When the plate comes into abutment against the front face 4 of the injector, it lies immediately above the recess 24, and the peg 16 lies immediately above the housing 20 of the pusher.

Figure 7:
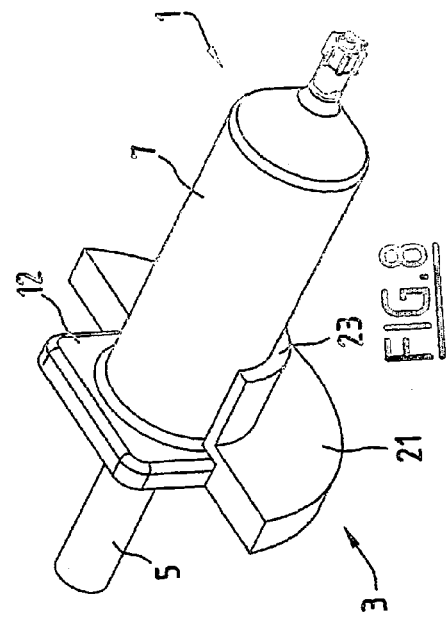
FIGS. 7 and 8 are views analogous respectively to FIGS. 5 and 6, after the syringe has been connected to the pusher.
Figure 6:
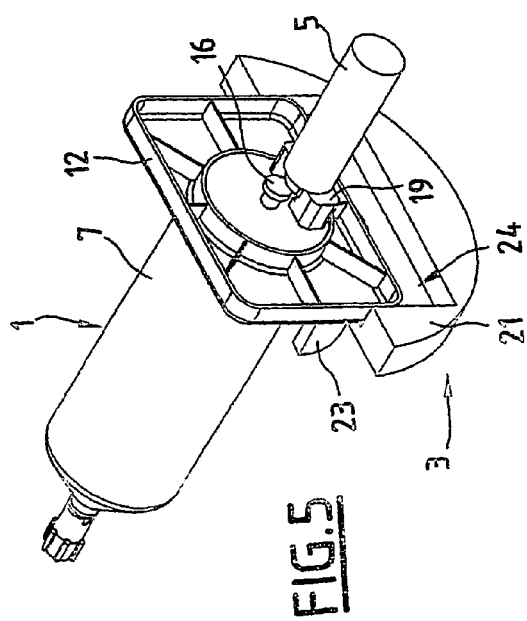
Figure 8:
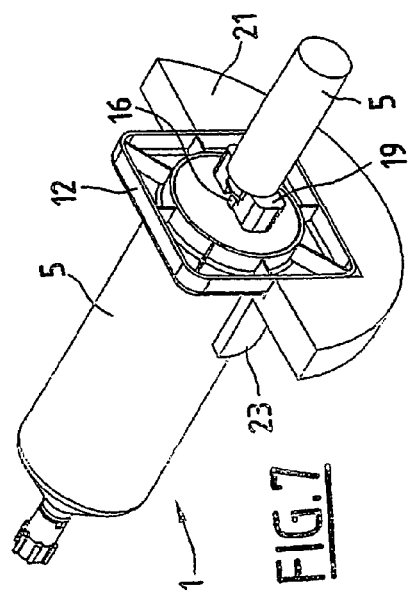

Merely moving the syringe downwards then simultaneously brings the bottom portion of the plate 12 into the recess 24, the bottom portion of the syringe body 7 into the cradle 23, and the bottom portion of the peg 16 into the housing 20 (FIGS. 7 and 8).

Thus, the syringe is prevented from moving in translation by the faces 4 and 27, its body is supported by the cradle 23, and the peg 16 is connected in both driving directions to the head of the pusher 19. No other moving part for securing the syringe is needed.

It is thus possible to begin actuating the pusher in operational manner immediately.

In order to disconnect the syringe from the injector, it suffices to retract the pusher, to raise the syringe, and then, once the plate is fully extracted from the recess 24, to extract the syringe in a forward direction.

The angiographic injection system of FIGS. 9 to 12 differs from that of FIGS. 1 to 8 in the following points only.

Firstly, the syringe plate is replaced by two diametrically-opposite radial tabs 30.

Secondly, the recess 24 of the support device is constituted by a central portion 31 having a circularly-arcuate section extending the inside surface of the cradle 23, and by two diametrically-opposite horizontal notches 32 opening out into the central portion 31 and substantially complementary in shape to the bottom halves of the tabs 30. Each surface 33 for connecting a notch 32 to the central portion 31 is a convex curved surface (FIG. 11).

The syringe is secured to the injector as described above with reference to FIGS. 1 to 8, except that it is the bottom surfaces of the two tabs 30 that slide on the top surfaces of the cradle 23. Once again, connection of the peg 16 with the front pusher head 19 is obtained simultaneously.

Figure 14:
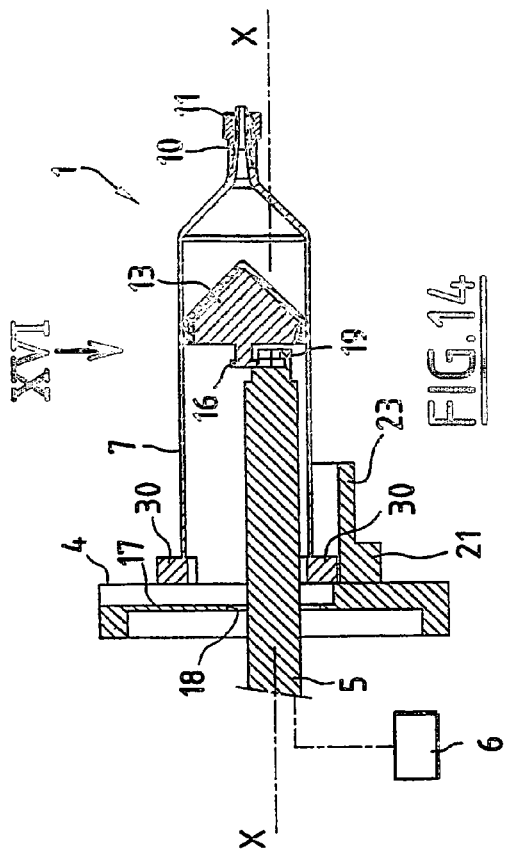
FIGS. 13 to 16 are views corresponding respectively to FIGS. 9 to 12, after the syringe and the pusher have been disconnected.
Figure 16:
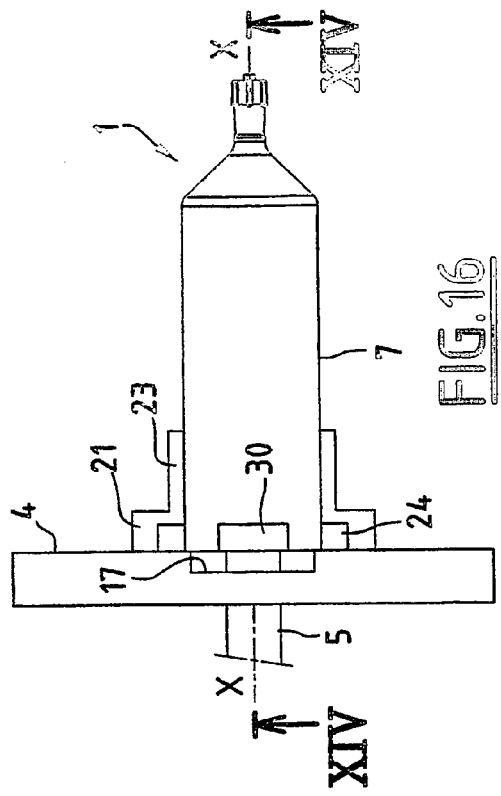
Figure 13:
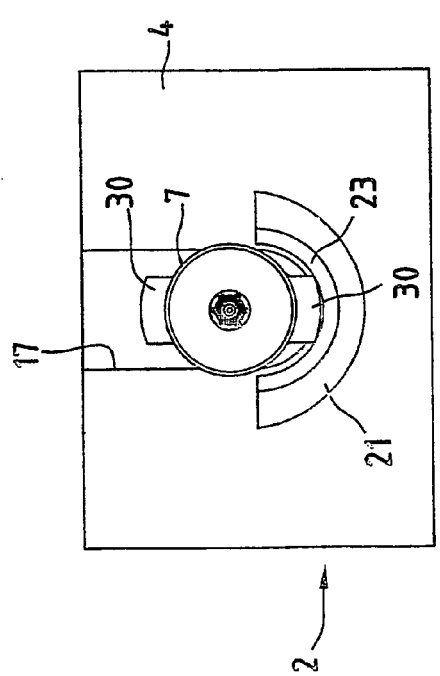
Figure 15:
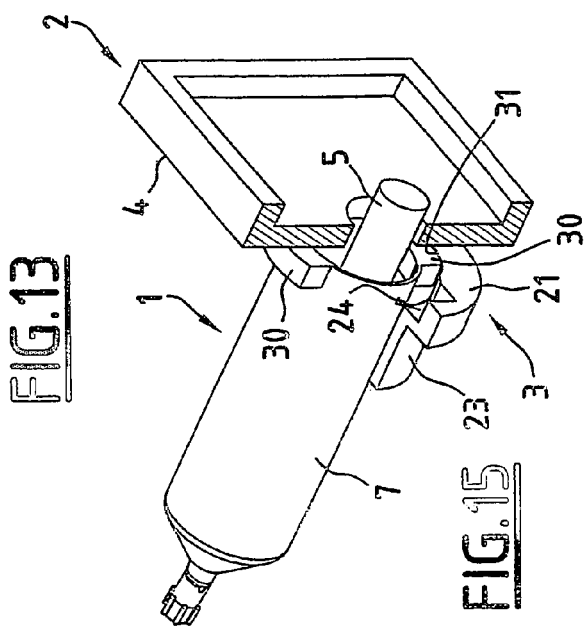

In order to disconnect the syringe from the injector, the syringe body 7 is grasped and turned through 90°. One of the tabs 30 then co-operates with the bottom of the notch 31 and then with the associated convex surface 33, which forms a camming slope, thereby causing the syringe to be raised and consequently disconnecting the piston from the pusher 5. The two tabs are thus brought into a generally vertical plane (FIGS. 13 to 15), and the syringe can be simply pulled away forwards. Thus, the tabs 3' and the convex surface 33 define a means for releasably coupling the piston 13 to the pusher front head 19.

This variant makes it easier to disconnect the piston from the pusher. Furthermore, the configuration with two tabs and corresponding front abutment surfaces 27 of the support device enable the syringe to be withdrawn forwards even if the pusher is engaged in the syringe body, without there being any need to begin by moving the pusher over a withdrawal stroke.

The invention claimed is:

1. An angiographic injection system comprising:
   an angiographic injector having an axially-movable pusher having a front end;
   at least one angiographic syringe including a body provided with an outwardly-projecting projection at a proximal end of the body, a cross-section of the body at said projection being non-circular, said projection being constituted by two diametrically-opposite tabs, the syringe also comprising a piston movably disposed in the body, said piston being provided with structure for releasably coupling the piston to a front head of the pusher; and
   support device secured to the front face of the injector for securing the syringe to the front face of the injector,
   the support device including a recess that is open in a reception direction and presents firstly a non-circular cross-section that is complementary to a portion of the cross-section of the syringe body at the location of said projection, and secondly a front face for coming into abutment against said projection, the device being extended forwards by a cradle for supporting the syringe body, wherein the recess includes a central portion that is circularly arcuate in cross-section, and that is extended by two diametrically-opposite notches, each said projection being adapted to be received in one of the notches in such a manner as to be positioned thereby, wherein said central portion is flush with the inside surface of the cradle,
   wherein, starting from the position in which the syringe is secured, the system is arranged in such a manner that turning the syringe through 90° causes it to be lifted by one of the tabs cooperating with the bottom of the associated notch, then with said central portion, whereby the piston and the pusher are disconnected, the syringe then being removable in a forward direction, even if the pusher is engaged inside the body of the syringe, by a sliding movement of said one tab, along said central portion, and then along said inside surface of the cradle.

2. The angiographic injection system according to claim 1, wherein said reception direction is directed upwardly.

3. The angiographic injection system according to claim 1, wherein each notch is connected to the central portion via a cam-forming convex curved surface.

4. The angiographic injection system according to claim 1, wherein the recess is rearwardly open, and wherein the front face of the injector forms the rear face of the recess.

5. The angiographic injection system according to claim 1, wherein the head of the pusher and the piston comprise between them an undercut peg and a slot that is open in said reception direction or in the opposite direction such that when the pusher is in the retracted position, putting the projection of the syringe into place in the recess by moving in the direction opposite to said reception direction causes the peg to be inserted into the slot.

* * * * *